United States Patent
Xi et al.

(10) Patent No.: US 9,037,236 B2
(45) Date of Patent: May 19, 2015

(54) METHOD AND SYSTEM TO SELECT A NEUROSTIMULATION SYSTEM CONFIGURATION BASED ON CARDIAC RHYTHM FEEDBACK

(75) Inventors: Cecilia Qin Xi, San Jose, CA (US); Lanitia Ness, Los Angeles, CA (US); Stuart Rosenberg, Castaic, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/537,757

(22) Filed: Jun. 29, 2012

(65) Prior Publication Data
US 2014/0005739 A1    Jan. 2, 2014

(51) Int. Cl.
*A61N 1/36* (2006.01)
*A61N 1/365* (2006.01)
*A61B 5/0452* (2006.01)
*A61N 1/362* (2006.01)
*A61B 5/0468* (2006.01)
*A61B 5/046* (2006.01)

(52) U.S. Cl.
CPC ........ *A61N 1/36592* (2013.01); *A61N 1/36142* (2013.01); *A61N 1/3621* (2013.01); *A61N 1/36585* (2013.01); *A61B 5/0452* (2013.01); *A61B 5/0468* (2013.01); *A61N 1/36185* (2013.01); *A61N 1/36139* (2013.01); *A61B 5/046* (2013.01)

(58) Field of Classification Search
None
See application file for complete search history.

(56) References Cited

U.S. PATENT DOCUMENTS

| | | | |
|---|---|---|---|
| 5,824,021 A | 10/1998 | Rise | |
| 6,662,053 B2 | 12/2003 | Borkan | |
| 7,162,304 B1 | 1/2007 | Bradley | |
| 7,672,733 B2 | 3/2010 | Zhou et al. | |
| 2002/0022866 A1 | 2/2002 | Borkan | |
| 2005/0143779 A1* | 6/2005 | Libbus | 607/9 |
| 2005/0209655 A1* | 9/2005 | Bradley et al. | 607/48 |
| 2007/0150011 A1* | 6/2007 | Meyer et al. | 607/9 |

FOREIGN PATENT DOCUMENTS

EP    1 181 949 A2    2/2002

OTHER PUBLICATIONS

Armour JA, Randall WC, and Sinha S. Localized myocardial responses to stimulation of small cardiac branches of the vagus. Am J Physiol 228: 141-148, 1975.

Armour JA, Richer LP, Pagé P, Vinet A, Kus T, Vermeulen M, Nadeau R, and Cardinal R. Origin and pharmacological response of atrial tachyarrhythmias induced by discrete activation of mediastinal nerves in canines. Auton Neurosci 118: 68-78, 2005.

(Continued)

*Primary Examiner* — Michael Kahelin
(74) *Attorney, Agent, or Firm* — Steven M. Mitchell

(57) ABSTRACT

Methods and systems are provided to control a configuration of a neural stimulation (NS) system having an NS device coupled to an NS lead. The methods and systems change between configurations of the NS system and collect cardiac signals from a patient that are representative of cardiac rhythms experienced by the patient over a period of time and in connection with multiple NS configurations. The methods and systems derive, from the cardiac signals, characteristic values for at least one physiologic characteristic indicative of at least one of normal and abnormal cardiac rhythms in connection with the multiple NS configurations; and select, from the multiple NS configurations, an NS operating configuration to be used by the NS system based on the characteristic values.

38 Claims, 4 Drawing Sheets

(56) References Cited

OTHER PUBLICATIONS

Scherlag BJ, Yamanashi WS, Schauerte P, Scherlag MA, Sun YX, Hou Y, Jackman WM, and Lazzara R. Extravascular stimulation within the left pulmonary artery to induce slowing of heart rate and paroxysmal atrial fibrillation. Cardiovasc Res 54: 470-475, 2002.

Sharifov OF, Fedorov VV, Beloshapko GG, Glukhov AV, Yushmanova AV, and Rosenshtraukh LV. Roles of adrenergic and cholinergic stimulation in spontaneous atrial fibrillation in dogs. J Am Coll Cardiol 43: 483-490, 2004.

Cardinal R, Page P, Vermeulen M, et al. Spinal cord stimulation suppresses bradycardias and atrial tachyarrhythmias induced by mediastinal nerve stimulation in dogs. AJP Regul Integr Comp Physiol 2006; 291:R1369.

Bernstein SA, Wong B, Rooke R, et al. Spinal cord stimulation prevents tachypacing induced atrial fibrillation. Heart Rhythm 2011 (HRS Poster).

* cited by examiner

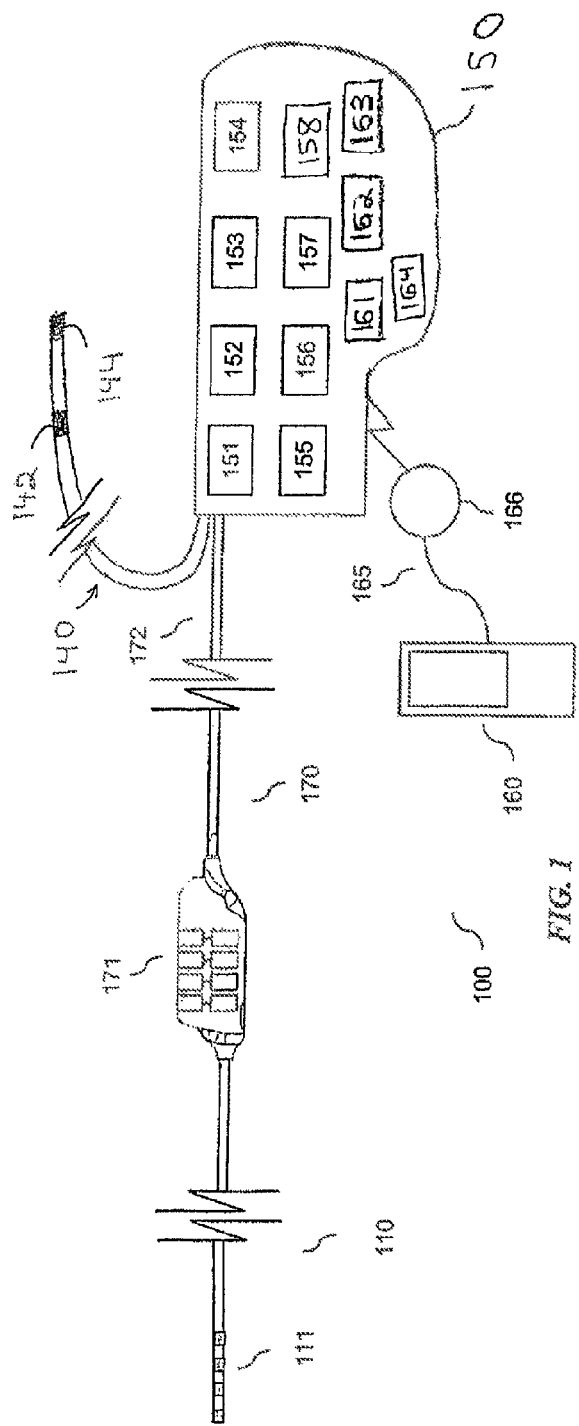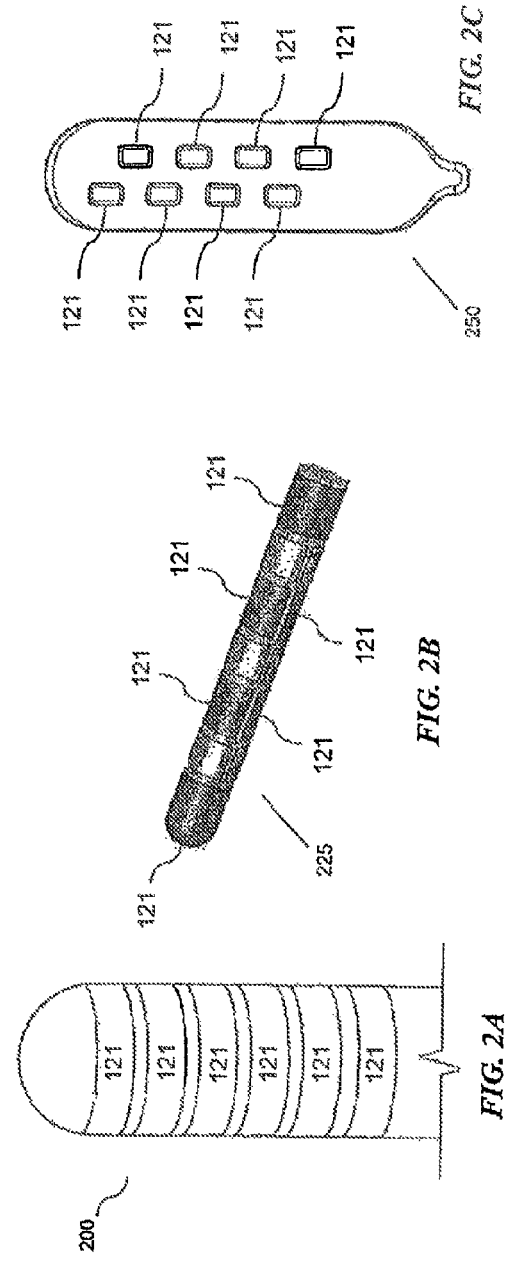

METHOD AND SYSTEM TO SELECT A NEUROSTIMULATION SYSTEM CONFIGURATION BASED ON CARDIAC RHYTHM FEEDBACK

BACKGROUND OF THE INVENTION

Embodiments of the present invention generally relate to neurostimulation systems and methods, and more particularly to restoring sinus rhythm through control of a neurostimulation configuration.

Neurostimulation systems (NS) are devices that generate electrical pulses and deliver the pulses to nerve tissue to treat a variety of disorders. Spinal cord stimulation (SCS) is the most common type of neurostimulation. In SOS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

NS and SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In NS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Spinal cord stimulation is commonly used to treat neuropathic pain. More recently, spinal cord stimulation has been considered as a treatment for various cardiac management applications. These may include angina, heart failure (HF), as well as bradycardia and atrial and ventricular tachyarrhythmias including atrial fibrillation (AF).

Literature has discussed the potential to use SCS to suppress bradycardia and tachycardia. Increasing extrinsic neuronal inputs to the intrinsic cardiac nervous system can initiate self-termination of episodes of atrial tachyarrhythmia (AT) and/or fibrillation (AF) in intact hearts without the need for concomitant programmed electrical stimulation of atrial muscle. However, the proposed electronic and physiologic mechanism to utilize SCS therapy to terminate AF or AT is a complex interaction of sympatholytic and vagotonic signaling. For example, the physiologic mechanism may include both inhibition of sympathetic outflow to the heart and stimulation of afferent fibers that trigger centrally-mediated parasympathetic reflex. However, thus far, no detailed models have been accepted as a complete and accurate description of the interaction of sympatholytic and vagotonic signaling. Hence, it is not yet known what types of NS configurations will yield a desired result for patients experiencing AF or AT.

SUMMARY

In accordance with an embodiment, a method is provided to control a configuration of a neural stimulation (NS) system having an NS device coupled to an NS lead. The method comprises changing between configurations of the NS system and collecting cardiac signals from a patient that are representative of cardiac rhythms experienced by the patient over a period of time and in connection with multiple NS configurations. The method derives, from the cardiac signals, characteristic values for at least one physiologic characteristic indicative of at least one of a normal and abnormal cardiac rhythm in connection with the multiple NS configurations. The method selects, from the multiple NS configurations, an NS operating configuration to be used by the NS system based on the characteristic values.

The collecting operation may be performed over an extended period of time to obtain long-term diagnostic trends, thereby enabling the selecting operation to assess whether a long-term improvement is achieved when utilizing one or more of the NS operating configurations. The collecting operation may be performed over an extended period of time to obtain a trend for AT/AF burden, where the selecting operation is based on the trend for AT/AF burden.

The changing operation is performed automatically at predetermined periodic intervals, with the physiologic characteristic representing AT/AF burden such that the deriving operation records the characteristic values for AT/AF burden exhibited during each of the predetermined periodic intervals. The selecting operation may include identifying a select characteristic value that satisfies a predetermined condition and determining one of the NS configurations that is associated with the select characteristic value. The method may further comprise maintaining a one to one relation between the characteristic values that are derived, and at least one of the NS configurations that was operative at the time when the cardiac signals associated with the characteristic values were collected.

The method may further comprise determining that the cardiac rhythm exhibits an arrhythmia, and directing the NS device to begin operation with at least one of the NS configurations in response to the determination that the cardiac rhythm exhibits an arrhythmia.

The method may include determining a characteristic value for at least one of an acute cardiac rhythm characteristic and a chronic cardiac rhythm characteristic. The deriving operation may include determining a characteristic value for at least one of the following physiologic characteristics: restoration time, R-R interval, PP interval, R-wave regularity, P-wave regularity, dominant frequency of atrial fibrillation (AF), AF rate, AF regularity, Peak atrial rate, and a ratio of a number of ventricular events per set of atrial events (i.e. AV conduction ratio).

The changing operation may include switching between at least one of i) first and second electrode combinations, ii) first and second stimulus patterns, and iii) first and second active electrode placements, utilized to deliver an NS therapy from the NS lead.

The changing operation may include switching between first and second stimulus patterns utilized to deliver an NS therapy from the NS lead. The changing operation may include changing a configuration value of at least one configuration parameter from the set of configuration parameters that includes stimulus phase, frequency, pulse width, pulse amplitude, number of active electrodes, active electrode pattern, active electrode position within an electrode array, active electrode placement with respect to a reference anatomy.

The method may further comprise sensing the cardiac signals, the cardiac signals representing one of intrathoracic electrogram signals, electrocardiogram signals, heart sound signals, blood pressure signals, and blood oxygen content signals.

In accordance with an embodiment, a neural stimulation (NS) system is provided that comprise an NS device coupled to an NS lead, memory configured to save multiple NS configurations, and a controller configured to direct the NS device to operate in at least a sub-set of the multiple NS configurations. Inputs are configured to receive cardiac signals that are collected from a patient. The cardiac signals are representative of cardiac rhythms experienced by the patient over a period of time during which at least the sub-set of the multiple NS configurations is utilized. A cardiac signal analysis (CSA) module is configured to derive, from the cardiac signals, characteristic values (CVs) for at least one physiologic characteristic indicative of at least one of normal and abnormal cardiac rhythms that occur while the NS device operates in at least the sub-set of the multiple NS configurations. A CV analysis module is configured to analyze the CVs and select, from the multiple NS configurations, an NS operating configuration to be used by the NS system based on the characteristic values.

The inputs receive cardiac signals over an extended period of time and the CV analysis module analyzes the CVs to obtain long-term diagnostic trends. The CV analysis module is configured to assess whether a long-term improvement is achieved when utilizing one or more of the NS operating configurations. The CV analysis module analyzes AT/AF burden experienced by the heart and obtains a trend for AT/AF burden. The CV analysis module may select the NS operating configuration based on the trend for AT/AF burden.

The controller changes from one of the NS configurations to another NS configuration based on at least one of i) automatically after a predetermined period of time and ii) the physiologic characteristic of the cardiac signals. The physiologic characteristic may represent AT/AF burden. The memory records the characteristic values for AT/AF burden exhibited during each of the predetermined periodic intervals. The CV analysis module may identify a select characteristic value that satisfies a predetermined condition and determines one of the NS configurations that is associated with the select characteristic value. The memory maintains a one to one relation between the characteristic values that are derived and one of the NS configurations that was operative at the time when the cardiac signals associated with the characteristic values were collected. The controller may be configured to direct the NS device to begin operation with one of the NS configurations in response to a determination that the cardiac rhythm exhibits an arrhythmia.

Embodiments are described herein that address the complexity of the therapeutic mechanism, for applications such as arrhythmia prevention and termination, by affording cardiac rhythm feedback to aid in determining NS lead placement and configuration, to aid in troubleshooting NS lead migration issues, and to aid in assessing the patient's response to NS treatment acutely.

In accordance with one embodiment, a CRMD device can provide real-time or stored EGM as feedback of cardiac rhythm if the normal sinus rhythm is restored after NS application to guide optimization of NS lead placement and configuration (including all programmable stimulation parameters), troubleshoot lead migration issues, and assess the patient's response to treatment and allow adjustment of NS dosage and parameters. In addition, long-term diagnostics trends or episodes can also be used to monitor the effect of NS chronically. Auto re-programming of the NS configurations can be applied based on the cardiac rhythm feedback.

BRIEF DESCRIPTION OF THE DRAWINGS

FIG. 1 depicts a neurological stimulation system that generates electrical pulses for application to nervous tissue of a patient according to one embodiment.

FIGS. 2A-2C respectively depict stimulation portions for inclusion at the distal end of a lead according to some representative embodiments.

DETAILED DESCRIPTION

Figure 3:
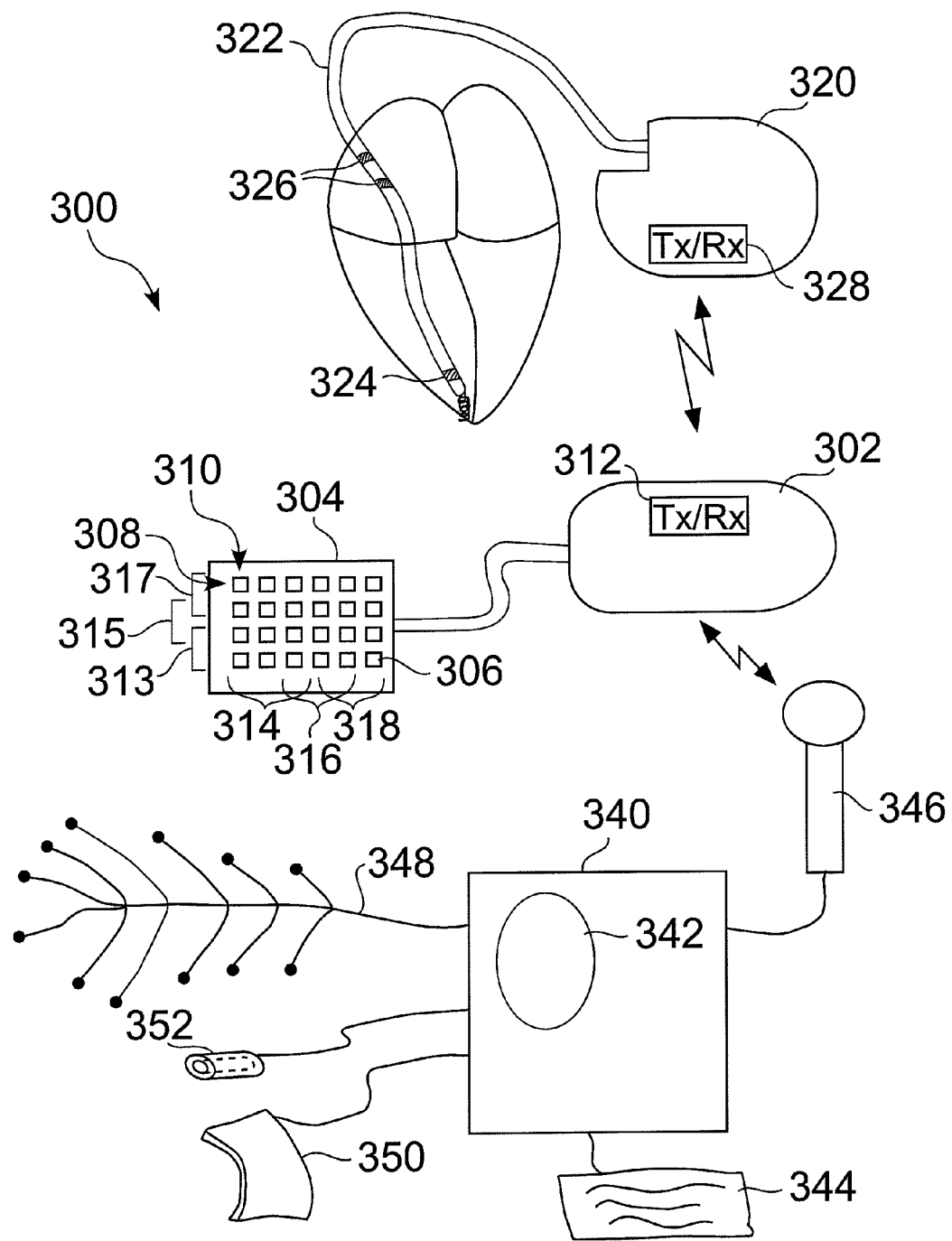
FIG. 3 illustrates a block diagram of an exemplary system 300 that may be implemented in accordance with an embodiment.

Embodiments described herein include systems and methods that utilize acute cardiac rhythm feedback to select neurostimulation systems (NS) configurations. The methods and systems record and analyze the manner and degree of changes in a patient's cardiac rhythm that are caused by NS stimulation therapy. Multiple NS lead locations, NS therapies, electrode configurations and the like are utilized to deliver NS stimulation in various manners intended to affect a patient's cardiac rhythm. When an NS lead location, therapy, and/or electrode combination is selected, the system and method wait a predetermined period of time before recording and analyzing the manner and degree of changes in the patient's cardiac rhythm in order to provide a transition period in which the cardiac rhythm changes or reacts to the NS stimulation.

The cardiac rhythm may be monitored in various manners. For example, real-time EGM or IEGM signals may be collected by an implantable medical device (IMD), a portable external device worn by the patient, a home monitoring device or an external programmer. The IMD may be an NS device, or a cardiac-related device, such as a pacemaker, ICD, CRT, CRM device and the like. The system and method record and identify an amount of time between i) when a current NS therapy begins delivery and ii) the cardiac signals return to a "normal" sinus rhythm (referred to as "restoration time"). A "normal" sinus rhythm may represent a rhythm in which one or more predetermined characteristics of the rhythm fall within programmed limits that are preset or programmed by the user. By way of example, restoration time may refer to the amount of time between when an NS therapy is delivered and when the R-R interval returns to within a programmed R-R range, thereby designating a restored sinus rhythm. Alternatively, other physiologic characteristics or features may be used to indicate when/whether the current NS configuration/position is successful in impacting an AF episode to change and/or terminate.

There may be at least two time constants associated with an amount of time that it takes for arrhythmia-related electrophysiology changes to occur in response to NS therapies and other neurostimulation based therapies. One time constant relates to the amount of time needed after delivery of an NS therapy before stabilization of local circuit neurons of the intrinsic cardiac nervous system (ICN). The ICN time constant may occur immediately (order of 1-3 seconds) given that firing of any given input to the ICN is stochastic and typically occurs once every one-to-several cardiac cycles. Many such nerve firings are integrated by ICN when considering the locally processed response. The second time constant relates to an amount of time that it takes for triggering of the centrally-mediated reflexes (TMR) to occur. The TMR time constant may occur on the order of tens of seconds after initiation of an NS therapy. Steady state has been reached by several minutes of NS stimulation, which is when most reported measurements of NS therapy effects on electrophysiology have been recorded. While the absolute time course of steady state may vary somewhat, after several minutes steady state is achieved. Optionally, steady state may be achieved in a shorter time period such as in several 10s of seconds as opposed to several minutes. The time period for the TMR to achieve steady state may differ for different NS configurations.

Embodiments described herein use the restoration time as well as other physiologic characteristics of the restored sinus rhythm such as rate, signal amplitude etc. as compared to the patient's sinus rhythm taken previously to determine which NS configuration, placement, and intensity combination achieves a desired level of NS effectiveness. As one example, the preferred NS configuration is the one that results in the fastest restoration time and with an ensuing sinus rate closest to a programmed rate or to the patient's average resting heart rate. Alternatively, features during the transition period such as ventricular response rate and rate regularity can be used to determine a select NS configuration or placement. The selection criteria may be predetermined by the user manually or automatically such as restoration time less than X min, restored R rate slower than Y bpm for atrial tachyarrhythmia (or greater than Z bpm for bradycardia). The selection criteria may also have relative criteria, for example, to select from amongst a number of configurations with restoration time less than X min, that configuration with the shortest restoration time. The restoration time and restored sinus rhythm characteristics are stored in the NS device and used as a reference for comparison with future device parameter changes.

In some cases, complete restoration of sinus rhythm may not be achievable. When this happens, a secondary metric, preferably ventricular rate or ventricular regularity (or a weighted combination thereof), is used to determine the select NS configuration to use. Alternately to ventricular rate and regularity, the mean atrial rate (minimize) or peak atrial rate (minimize) or atrial regularity (maximize) or atrial EGM fractionation (minimize) or a weighted combination thereof, may be used to determine the optimal NS configuration. If NS therapy is not already enabled, detection of the onset of an AT/AF episode may be used to enable NS therapy and potentially terminate the event.

Embodiments are also described for methods and systems that utilize chronic cardiac rhythm feedback. Instead of using real-time EGMs, this application utilizes long-term diagnostic trends such as AT/AF burden to assess the long-term improvement with certain NS configurations. An automatic searching algorithm can be applied such as switching to each of the different NS configurations for W weeks and record the corresponding AT/AF burden. After the end of the search, the methods and systems determine which NS configuration is desired to restore and maintain sinus rhythm. Chronic cardiac rhythm feedback can also be used to automatically adjust the current NS parameters such as the pacing amplitude, duration and pacing dosage per day etc.

Alternately, each given NS configuration may be programmed for H hours (instead of W weeks) and recorded AT/AF burden trends are associated with the respective NS configuration at the time. Different NS configurations are programmed in a semi-randomized order to ensure that each configuration is used at different time periods throughout the day. The cumulative AT/AF burdens throughout the various trials are summed or averaged for each respective configuration. The best NS configuration is chosen as the one with the lowest cumulative AT/AF burden. Further, different configurations may have differential efficacy at specific times of day or during active vs rest states, etc. In such case (as would likely be computed by logistic regression run on a networked server such as Merlin.net), dedicated NS configurations deemed "best" at the particular time of day or particular patient status may be programmed in cycle mode or dynamically in order to provide ongoing optimization of NS anti-arrhythmic therapy.

FIG. 1 depicts a neurological stimulation system 100 that generates electrical pulses for application to nervous tissue of a patient according to one embodiment. For example, system 100 may be adapted to stimulate spinal cord tissue, peripheral nerve tissue, deep brain tissue, cortical tissue, or any other nervous tissue within a patient's body.

System 100 includes implantable NS device 150 that is adapted to generate electrical pulses for application to the nerve system of a patient. Implantable NS device 150 typically comprises a metallic housing that encloses controller 151, pulse generating circuitry 152, charging coil 153, battery 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the NS device 150 for execution by the microcontroller or processor to control the various components of the device.

The NS device 150 may comprise a separate or an attached extension component 170. If extension component 170 is a separate component, extension component 170 may connect with the "header" portion of NS device 150. If extension component 170 is integrated with NS device 150, internal electrical connections may be made through respective conductive components. Within NS device 150, electrical pulses are generated by pulse generating circuitry 152 and are provided to switching circuitry 157. The switching circuit connects to outputs of NS device 150. Electrical connectors (e.g., "Bal-Seal" connectors) within connector portion 171 of extension component 170 or within the NS DEVICE header may be employed to conduct the stimulation pulses. The terminals of one or more stimulation leads 110 are inserted within connector portion 171 or within the NS DEVICE header for electrical connection with respective connectors. Thereby, the pulses originating from NS device 150 are provided to stimulation lead 110. The pulses are then conducted through the conductors of lead 110 and applied to tissue of a patient via electrodes 111. Any suitable known or later developed design may be employed for connector portion 171.

For implementation of the components within NS device 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within NS device 150. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulation material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

The NS device 150 includes one or more inputs 161 that are configured to receive cardiac signals. A sensing lead 140 is connected to the NS device 150. The sensing lead 140 collects cardiac signals from a patient and supplies the cardiac signals to the inputs 161. Optionally, the inputs 161 may also receive cardiac signals from a separate implantable device and/or from an external device. The cardiac signals are representative of cardiac rhythms experienced by the patient over a period of time and in connection with multiple NS configurations. The sensing lead 140 includes sensors 142 and 144 that sense cardiac activity and generate cardiac signals associated therewith. As one example, the sensors 142, 144 may sense IEGM signals. Optionally, the sensing lead 140 may sense ECG signals, heart sound signals, blood pressure signals, blood oxygen content signals and the like.

The NS device 150 may include a cardiac arrhythmia analysis (CAA) module 158 that analyzes cardiac signals to identify the occurrence of an arrhythmia. For example, the CAA module 158 may detect onset and/or termination of various arrhythmias such as atrial fibrillation (AF), atrial tachy-cardia (AT), ventricular fibrillation (VF), ventricular tachy-cardia (VT), ST segment shift, and the like. Alternatively, the NS device 150 may receive a communication from an external device or another implantable device indicating that onset of an arrhythmia has been detected, an AT has changed to AF, and/or an arrhythmia has been terminated. For example, the NS device 150 may receive the communication from an implantable pacemaker, ICD, CRT, defibrillator, CRM device and the like. Optionally, the NS device 150 may receive the communication from an external home monitor, external programmer, external ECG monitor and the like. Optionally, the controller 151 may be configured to direct the NS device 150 to begin operation in a select one of the NS configurations in response to a determination that the cardiac rhythm exhibits an arrhythmia. The select NS configuration may be preprogrammed or based on the type of arrhythmia detected.

The NS device 150 includes memory 164 that is configured to save multiple NS configurations. The memory 164 maintains a one to one relation between the characteristic values that are derived and a one of the NS configurations that was operative at the time when the cardiac signals associated with the characteristic values were collected.

The NS device 150 includes a cardiac signal analysis (CSA) module 162 that is configured to derive, from the cardiac signals, characteristic values (CVs) for at least one physiologic characteristic indicative of at least one of normal and abnormal cardiac rhythms that occur while the NS device operates, at different time intervals, in at least the sub-set of the multiple NS configurations. The CSA module 162 determines a characteristic value for at least one of an acute cardiac rhythm characteristic and a chronic cardiac rhythm characteristic. The CSA module 162 determines a characteristic value for at least one of the following physiologic characteristics: restoration time, R-R interval, P-P interval, R-wave regularity, P-wave regularity, dominate frequency of atrial fibrillation (AF), AF rate, AF regularity, Peak atrial rate, and a ratio of a number of ventricular events per set of atrial events.

The NS device 150 also includes a CV analysis module 163 that is configured to analyze the CVs and select, from the multiple NS configurations, an NS operating configuration to be used by the NS system based on the characteristic values. The CV analysis module 163 identifies a select characteristic value that satisfies a predetermined condition and determines a one of the NS configurations that is associated with the select characteristic value.

The inputs 161 may receive cardiac signals over an extended period of time, in which case the CV analysis module 163 analyzes the CVs to obtain long-term diagnostic trends. The CV analysis module 163 is configured to assess whether a long-term improvement is achieved when utilizing one or more of the NS operating configurations. The CV analysis module 163 may analyze AT/AF burden experienced by the heart and obtain a trend for AT/AF burden. The CV analysis module 163 selects the NS operating configuration based on the trend for AT/AF burden.

The controller 151 changes the NS configuration by switching between at least one of i) first and second electrode combinations, ii) first and second stimulus patterns, and iii) first and second active electrode placements, utilized to delivery an NS therapy from the NS lead. Optionally, the controller 151 may change the NS configuration by switching between first and second stimulus patterns utilized to delivery an NS therapy from the NS lead. As one example, one of the first or second stimulus patterns could be "stimulus OFF". Hence, when an the IMD may identify a characteristic value for a physiologic characteristic(s) of interest and in response thereto trigger the NS device to switch from being inactive and monitoring to being active and delivering therapy. Optionally, the controller 151 may change the NS configuration by changing a configuration value of at least one configuration parameter from the set of configuration parameters that includes stimulus phase, frequency, pulse width, pulse amplitude, number of active electrodes, active electrode pattern, active electrode position within electrode array, active electrode placement with respect to a reference anatomy. The controller 151 changes from one of the NS configurations to another NS configuration based on at least one of i) automatically after a predetermined period of time and ii) the physiologic characteristic of the cardiac signals, the physiologic characteristic representing AT/AF burden, the memory recording the characteristic values for AT/AF burden exhibited during each of the predetermined periodic intervals.

FIGS. 2A-2C illustrate stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes"121. The term "segmented electrode" 121 is distinguishable from the term "ring electrode." As used herein, the term "segmented electrode" refers to an electrode 121 of a group of electrodes 121 that are positioned at the same longitudinal location along the longitudinal axis of a lead and that are angularly positioned about the longitudinal axis so they do not overlap and are electrically isolated from one another. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

Controller device 160 may be implemented to recharge battery 154 of NS device 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown).

The patient then places the primary coil 166 against the patient's body immediately above the secondary coil (not shown), i.e., the coil of the implantable medical device. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 153 by charging circuitry 156. Charging circuitry 156 may also communicate status messages to controller 160 during charging operations using pulse-loading or any other suitable technique. For example, controller 160 may communicate the coupling status, charging status, charge completion status, etc. Optionally, the controller 160 may operate as a "relay" by receiving cardiac signals from a separate implantable device and/or an external device and relaying/conveying the cardiac signals to the NS device 150.

External controller device 160 is also a device that permits the operations of NS device 150 to be controlled by user after NS device 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with NS DEVICE 150.

Controller device 160 preferably provides one or more user interfaces to allow the user to operate NS device 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of NS DEVICE 160 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. The NS device 150 modifies internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No, WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

FIG. 3 illustrates a block diagram of an exemplary system 300 that may be implemented in accordance with an embodiment. The system 300 includes an NS device 302 that is coupled to an NS lead 304. The NS lead 304 includes electrodes 306 that are arranged in a two dimensional array of rows 308 and columns 310. The electrodes 306 delivery NS therapies based on the current operating NS configuration.

The NS device 302 will activate different combinations of the electrodes 306, such as to electronically shift a placement where and configuration at which an NS therapy is delivered on a particular vertebra. For example, during NS configurations #1, #2 and #3, different electrode column combinations 314, 316 and 318, respectively, may be active. By moving between NS configurations, and thus active electrode column combinations 314, 316 and 318, the NS therapy can be delivered at different lateral or longitudinal positions along the vertebra relative to a lateral reference point. Similarly, the active electrode row combinations 313, 315 and 317 could be switched to shift a position of the NS therapy in a vertical direction up or down relative to a vertical reference point on a vertebra.

A separate implantable medical device (IMD) 320 is provided. The IMD 320 may be a pacemaker, ICD device, CRT device, other CRM device such as subcutaneous AF monitor, or other device configured to sense and/or deliver stimulus to cardiac tissue. The IMD 320 is coupled to a lead 322 that has a distal end that is configured to be inserted into one or more chambers of the heart. For example, the lead 322 may include a distal end with one or more electrodes 324 inserted into the right ventricle. The lead 322 may also include one or more electrodes 326 located in the right atrium. The electrodes 324 and 326 sense cardiac signals and may also deliver pacing and/or high voltage stimulus to the heart tissue. The IMD 320 includes a transmitter/receiver (Tx/Rx) 328 that is configured to communicate with the transmitter/receiver (Tx/Rx) 312 in the NS device 320. The Tx/Rx 328 may convey, among other things, cardiac signals sensed at the IMD 320 to the NS device 302. Optionally, the IMD 312 may analyze the cardiac signals sensed by the electrodes 324, 326 to identify onset, change between AT and AF, and/or termination of an arrhythmia, and then transmit a corresponding status command to the NS device 302 (e.g., AF onset detected, AF start time, AF termination detected, AF end time, AT onset detected, AT start time, AT termination detected, AT end time, ST segment shift and the like).

As a further option, the IMD 320 may sense cardiac signals, as well as analyze the cardiac signals to identify characteristic values (CVs) for the physiologic characteristic(s) of interest. For example, the IMD 320 may implement a cardiac signal analysis module (similar to the CSA module 162 in FIG. 1) to derive, from the cardiac signals, characteristic values for at least one physiologic characteristic indicative of at least one of normal and abnormal cardiac rhythms that occur while the NS device operates in at least the sub-set of the multiple NS configurations. When the IMD 320 calculates CVs, the Tx/Rx 328 would transmit the CVs to the Tx/Rx 312 of the NS device 302.

Optionally, the IMD 320 may also include a CV analysis module (similar to CV analysis module 163 in FIG. 1) to analyze the CVs and select, from the multiple NS configurations. When the IMD 320 analyzes CVs to select an NS configuration, the Tx/Rx 328 would transmit instructions to change the NS operating configuration and/or each new NS configuration to the NS device 302.

An external device 340 is shown in FIG. 3. The external device 340 may be a home monitoring device, a Holter monitor worn by the patient, an external IMD or NS programmer, an ECG monitor and the like. The external device 340 includes a display 342, an input keyboard 344, and a wand 346 used to communicate with the NS device 302 and the IMD 312. A surface electrode set 348 is joined to the external device 340 to collect ECG signals as cardiac signals. Optionally, a blood pressure cuff 350 and blood oxygen sensor 352 may be coupled to the external device 340 to sense blood pressure and blood oxygen content, respectively. The external device 340 may transmit cardiac signals from the surface electrode set 348, the blood pressure cuff 350 and/or blood oxygen sensor 352 to the NS device 302 through the wand 346.

The external device 340 may implement a cardiac signal analysis module (similar to the CSA module 162 in FIG. 1) to derive, from the cardiac signals, characteristic values for at least one physiologic characteristic indicative of at least one of normal and abnormal cardiac rhythms that occur while the NS device operates in at least the sub-set of the multiple NS configurations. When the external device 340 calculates CVs, the external device 340 transmits the CVs to the Tx/Rx 312 of the NS device 302 through the wand 346.

Optionally, the external device 340 may also include a CV analysis module (similar to CV analysis module 163 in FIG. 1) to analyze the CVs and select, from the multiple NS configurations. When the external device 340 analyzes CVs to select an NS configuration, the external device 340 transmits instructions to change the NS operating configuration and/or each new NS configuration to the NS device 302.

Figure 4:
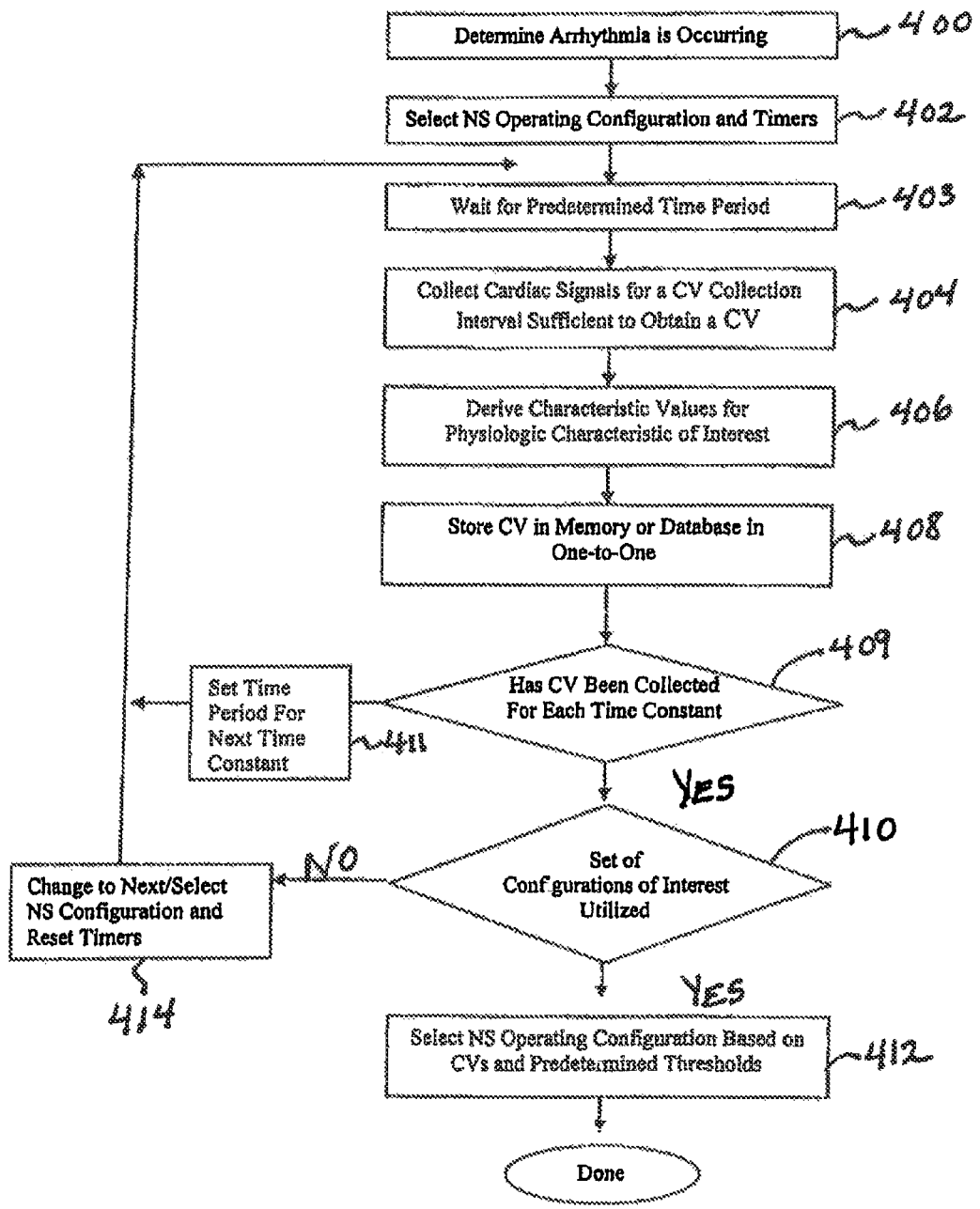
FIG. 4 illustrates a computer implemented method performed by the NS device, system, device or other computer system to control a configuration of an NS system in accordance with an embodiment.

FIG. 4 illustrates a computer implemented method performed by the NS device 150, 302, system 300, device 340 or other computer system to control a configuration of an NS system that includes an NS device and an NS lead. The method begins when a cardiac rhythm is identified to be abnormal. For example, when the NS system 100 includes sensors and the circuitry to monitor cardiac signals, the NS system 100 collects and analyzes the cardiac signals to determine when the heart is experiencing an arrhythmia, such as AF, AT, VT, and the like. The NS system 100 may also analyze the cardiac signals for other cardiac electrical disturbances, such as a ST segment shift and the like.

At 400, it is determined that an arrhythmia is occurring. At 402, an NS operating configuration is selected and one or more timers are set. The timers are associated with predetermined time periods in connection with time constants for certain arrhythmia related electrophysiology changes. For example, an initial NS operating configuration may be selected from a database of potential NS configurations. Optionally, the NS operating configuration may be selected based on the time of day, past physiologic behavior of the patient, type of arrhythmia and the like. As a further option, the NS operating configuration may be associated with a non-cardiac physiologic condition, such as to suppress pain and the like. The NS system begins to operate in accordance with the selected NS configuration, such as by delivering a programmed NS therapy once, continuously or at select intervals.

At 403, the method waits for a first one of the timers to expire after a predetermined time period. A currently selected NS operating configuration is utilized for the predetermined time period defined by the first timer. The timer or predetermined time period may be preset, programmable, or automatically determined by the NS device 302, IMD 320, or external device 340. The time period at 403 is set to afford the heart sufficient time to undergo certain changes in an arrhythmia that are in response to the current NS configuration. For example, the predetermined time period may be set to a common value for all arrhythmias (e.g., 5-10 minutes), after which it is expected that, to the extent that the current NS configuration could affect the heart rhythm, such effect will have occurred. Alternatively, different predetermined time periods may be set for different types of arrhythmias (e.g., 1 minute for AT, 5 minutes for AF, 20 minutes for ST segment shift).

At 404, the method collects cardiac signals, for a select period of time from a patient, that are representative of cardiac rhythms experienced by the patient over a predetermined period of time. The cardiac signals collected may represent one of intra-thoracic electrogram signals (IEGMs) and electrocardiogram signals (ECGs).

The cardiac signals are collected for a select CV collection interval that is sufficient to calculate a characteristic value, where such collection interval may be preset, programmed to a fixed duration, based on the behavior of the cardiac rhythm or automatically determined. For example, a physician may program the NS system to collect cardiac signals for a current NS operating configuration for a set collection interval (e.g. 1 minute when experiencing AT, 5-10 minutes or up to 1 hour when experiencing AF, CV 12 hours or 1 week when not experiencing ST segment shift). The method collects cardiac signals for the collection interval.

The NS device or another device/programmer may store the raw cardiac signals for the entire collection interval collected at 404 when the device/programmer has sufficient capacity. Alternatively, the NS device or other device/programmer may not store the raw cardiac signals for the entire collection interval. The cardiac signals are collected in real-time while the NS device is operating with an NS configuration that is currently selected. The collecting operation may be performed over an extended period of time to obtain long-term diagnostic trends. By performing long-term diagnostic trending, the method is able to assess whether a long-term improvement is achieved when utilizing one or more of the NS operating configurations. For example, the collecting operation may be performed over an extended period of time to obtain a trend for AT/AF burden, such as when the selecting operation is based on the trend for AT/AF burden.

At 406, the method derives, from the cardiac signals, characteristic values (CVs) for at least one physiologic characteristic of interest. The physiologic characteristic of interest is indicative of at least one of a normal and abnormal cardiac rhythm. As the process cycles through 404-410, the physiologic characteristic of interest is analyzed in connection with multiple NS configurations. In certain applications, the deriving operation includes determining a characteristic value associated with acute cardiac rhythms. For example, individual episodes of AF and AT represent acute cardiac rhythms. In other applications, the deriving operation determines a characteristic value associated with chronic cardiac rhythms, such as long term trends in an amount of AF or AT burden. As a further example, the deriving operation may include determining a characteristic value for at least one of the following physiologic characteristics: restoration time, R-R interval, P-P interval, R-wave regularity, P-wave regularity, dominate frequency of atrial fibrillation (AF), AF rate, AF regularity, ST segment shift, ST segment duration, Peak atrial rate, and a ratio of a number of ventricular events per set of atrial events. P-wave and R-wave regularity refer to a degree to which the P-P interval or the R-R interval remain constant over time, or within a certain level of deviation (e.g., within 1 or 2 standard deviation).

Various methods may be used to analyze the cardiac signal for the CV. For example, a peak detector may be used to detect peaks in the cardiac signal with a largest peak(s) being declared to be the R-wave peak. P-wave and ST-segment information may be determined by setting P-wave and ST-wave detection windows for time periods before and after the R-wave peak at which the P-wave and the ST-segment should occur. The method then analyzes the received cardiac signal during the detection window(s) for the feature(s) of interest (e.g., P-wave, ST-segments). Optionally, the P-wave and ST-segment may be identified as peaks exhibited within an amplitude percentage range of the amplitude of the R-wave. Optionally, morphology of the cardiac signal may be analyzed to derive the CV, such as through comparison to a prior cardiac signal, comparison to templates, and the like.

At 408, the method saves the characteristic values in memory database in a one to one relation between the characteristic values and a corresponding one of the NS configurations that was operative at the time when the cardiac signals associated with the characteristic values were collected. Individual CVs may be saved with the associated NS configuration. Alternatively, sets or ensembles of CVs may be combined to form a composite CV (e.g., an average CV). Optionally, the composite CVs may be formed by summing CVs over time. As a further option, when summing CVs over time, individual CVs may be weighted differently based upon various criteria such as the time of day, the reliability of the cardiac signal, the severity of the arrhythmia, the posture of the patient (e.g., stationary, exercising, sitting, lying down, etc.), the patient health status/condition, etc.

The predetermined time period (at 403) represents at least one time constant associated with arrhythmia related electrophysiology changes. There are more than one arrhythmia related electrophysiology change that occurs in response to NS therapy. The method of FIG. 4 may operate in connection with a single time constant (and thus predetermined time period). Alternatively, the method may operate in connection with multiple time constants (and thus predetermined time periods). For example, the method may operate in connection with at least two different arrhythmia related electrophysiology changes that have corresponding different time constants associated with an amount of time that it takes for arrhythmia related electrophysiology changes to occur in response to NS therapies.

At 409, the method determines whether the operations at 403-408 are to be repeated in connection with another timer or time constant of interest. As noted above, the arrhythmia may vary in response to more than one electrophysiology related time constant. For example, one time constant relates to the amount of time needed after delivery of an NS therapy before stabilization of local circuit neurons of the intrinsic cardiac nervous system (ICN). The ICN time constant may occur immediately (e.g., in the order of 1-3 seconds) given that firing of any given input to the ICN is stochastic and typically occurs once every one-to-several cardiac cycles. Many such nerve firings are integrated by ICN when considering the locally processed response. During a first iteration through the method of FIG. 4, following each new NS configuration, the method waits/delays at operation 403 for the duration of the ICN time constant. Thereafter, the method steps through the operations 404 to 408 to collect, analyze and save CV information following the ICN time constant.

Once CV information, associated with the ICN time constant is collected, flow moves to 409, where it is determined that another time constant exists, for which CV information should be collected. At 411, the method switches to monitor the second (longer) time constant which relates to an amount of time that it takes for triggering of the centrally-mediated reflexes (TMR) to occur. The TMR time constant may occur on the order of tens of seconds after initiation of an NS therapy. Steady state is reached after several minutes of NS stimulation, which is when most reported measurements of NS therapy effects on electrophysiology have been recorded. Once the method of FIG. 4 has stepped through the operations at 403-408 associated with the ICN time constant, the method may repeat the operations at 403-408 in connection with the TMR time constant. In particular, the method waits at operation 403 for the duration of the TMR time constant and thereafter steps through the operations 404 to 408 to collect, analyze and save CV information following the TMR time constant.

Hence, during a first iteration through the method of FIG. 4 for each new NS configuration, at 409, flow moves to 411 where the predetermined time period is set for the next time constant (e.g., the TMR time constant). Next flow returns to 403, where it waits/delays for the TMR time constant. Next, the operations at 404-408 are repeated to collect and analyze cardiac signals, and store CV information, associated with the TMR time constant. Once CV information is collected following each timer or predetermined time period of interest, flow moves to 410.

At 410, the method determines whether the operations at 404-408 should be repeated for additional potential NS configurations of interest. If so, flow moves to 414. If not, flow moves to 412. For example, memory or a database may save one or more sets of programmed NS configurations. For example, the set may include 20 NS configurations, where configurations 1-5 use a single first combination of electrodes, a first therapy type and 5 different stepped amplitudes. Configurations 6-10 may use a single second combination of electrodes, the same first therapy type and the same 5 different stepped amplitudes. Configurations 6-10 may use a single third combination of electrodes, the same first therapy type and the same 5 different stepped amplitudes. Alternatively, each NS configuration may include a different combination of electrodes that are selected to step spatially (e.g., laterally or longitudinally) across the vertebra on which the lead is positioned.

Optionally, at 410, the method may also determine whether a sufficient amount of data (e.g., cardiac signals) have been obtained in connection with each potential NS configuration. For example, after collecting cardiac signals and deriving characteristic values for each of ten potential NS configurations, it may be determined that too few cardiac signals and characteristic values were determined in connection with the second and/or fifth NS configurations, or that too much variation exists between the cardiac signals and characteristic values associated with one NS configuration. When it is determined that more cardiac signals and characteristic values are needed for one or more given NS configurations, flow moves to 414.

At 414, the method changes the configuration of the NS system to a new or selected (e.g. repeated) NS configuration from the set or database of potential NS configurations. At 414, the method also resets the timers for each time constant of interest. Thereafter, cardiac signals are collected from the heart, and characteristic values are determined for the physiologic characteristic(s), while the NS system operates using the new/repeated NS configuration. Optionally, the changing operation may be performed automatically at predetermined periodic intervals. When the physiologic characteristic represents AT/AF burden, the deriving operation records the characteristic values for AT/AF burden exhibited during each of the predetermined periodic intervals. The changing operation may include switching between at least one of i) first and second electrode combinations, ii) first and second stimulus patterns, and iii) first and second active electrode placements, utilized to delivery an NS therapy from the NS lead. Optionally, the changing operation may include switching between first and second stimulus patterns utilized to deliver an NS therapy from the NS lead. The set of configuration parameters that includes stimulus phase, frequency, pulse width, pulse amplitude, number of active electrodes, active electrode pattern, active electrode position within electrode array, active electrode placement with respect to a reference anatomy.

At 412, the method selects, from the multiple NS configurations, an NS operating configuration to be used by the NS system based on the derived characteristic values. To perform the selection, the method identifies a selected characteristic value that satisfies a predetermined condition and then determines one of the NS configurations that is associated with the selected characteristic value. Optionally, the selection includes identifying a selected characteristic value that satisfies a predetermined condition and determining one of the NS configurations that is associated with the selected characteristic value. Optionally, the trend during a selected NS configuration may be compared to a baseline trend when no NS configuration is used.

Figure 5:
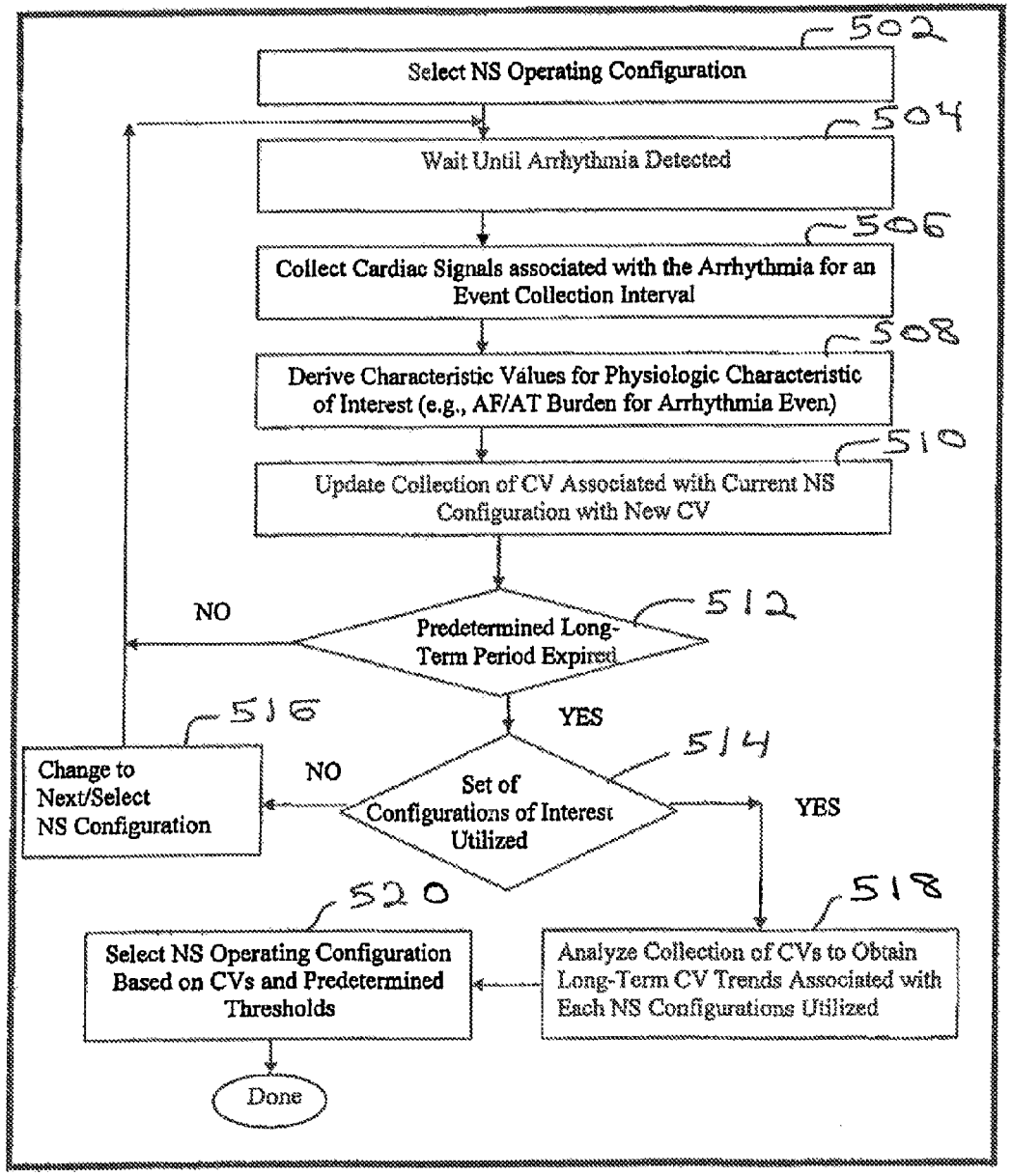
FIG. 5 illustrates a computer implemented method performed by one or more of the devices and systems described herein, to control a configuration of an NS system in connection with chronic cardiac rhythm feedback in accordance with an embodiment.

FIG. 5 illustrates a computer implemented method performed by one or more of the devices and systems described herein, to control a configuration of an NS system in connection with chronic cardiac rhythm feedback. The method of FIG. 5 uses long term diagnostic trends (e.g. multiple weeks, multiple months, multiple years), instead of real-time feedback, to assess whether longer term improvement in cardiac rhythm management can be achieved with certain NS configurations.

The method begins at 5402 wherein an NS operating configuration is selected. For example, an initial NS operating configuration may be selected from a memory database of potential NS configurations. Optionally, the NS operating configuration may be selected based on the time of day, neurologic therapy, past physiologic behavior of the patient, type of arrhythmia and the like.

At 504, the method waits until an arrhythmia is detected from the cardiac signals.

At 506, the method collects cardiac signals that are associated with the arrhythmia for an event collection interval. The cardiac signals may be directly measured by the NS device 150 through one or more sensors 142, 144 electrically coupled to the NS device 150. Alternatively or in addition, the cardiac signals may be wirelessly transmitted to the NS device 302 from another IMD 320 or from an external device 340. The collection at 506 may or may not store a raw ECG, IEGM or other signal as the cardiac signal. Instead, the collection operation at 506 may store, as the cardiac signal, summary data describing one or more physiologic characteristics of interest for an arrhythmia cardiac event.

Optionally, the collection at 506 may store ECG, IEGM or other signals intermittently for short intervals as the cardiac signal, such as when an IMD 150, 302, 320 detects onset of an arrhythmia and/or detects termination of the arrhythmia. Alternatively, the collection at 506 may store ECG, IEGM or other signals continuously from onset until termination of the arrhythmia. As a further option, the collection at 506 may be may store ECG, IEGM or other signals continuously for a predetermined period of time.

At 508, the method derives, from the cardiac signals, CVs for at least one physiologic characteristic of interest. For the method of FIG. 5, the physiologic characteristic of interest may exhibit a long term trend, such as AF burden, AT burden, ST segment shift and the like. The deriving operation includes determining a characteristic value associated with chronic cardiac rhythms. As a further example, the deriving operation may include determining a characteristic value for at least one of the following physiologic characteristics: restoration time, R-R interval, P-P interval, R-wave regularity, P-wave regularity, dominate frequency of atrial fibrillation (AF), AF rate, AF regularity, VT rate, ST segment shift, ST segment duration, Peak atrial rate, and a ratio of a number of ventricular events per set of atrial events.

At 510, a collection of CVs associated with the current NS configuration is updated. For example, if a current NS configuration is scheduled to be maintained for 1 week, and the physiologic characteristic of interest is AF burden, then each time an AF episode occurs the associated CV will be separately stored or added to a cumulative AF burden.

At 512, after the arrhythmia ends, the method determines whether the current NS configuration should be maintained. For example, when a predetermined long-term period of time ends (e.g., 1 week, 1 month), at 512 the method would determine to change the NS configuration. Otherwise, flow returns to 504 where the method waits for the next arrhythmia to occur. In this manner, the process of 504-510 repeats to record a CV for each arrhythmia episode and update the collection of CVs for a current NS configuration. For example, over a week period of time, the NS system may operate in a first NS configuration during which the patient experiences 15 AF episodes. The CV or CVs associated with each of the 15 AF episodes are determined and recorded to form a one week trend associated with an amount of AF burden experienced by the patient over the week period (e.g. the amount of time experiencing AF).

When the predetermined time period ends, flow moves from 512 to 514. At 514, the method determines whether additional NS configurations should be used. If so, flow moves to 516 where the NS configuration is switched to a new or select (e.g., repeat) NS configuration. The process of 502-514 repeats for an extended period of time (e.g., several days, weeks or months) to record a CV for each arrhythmia and each NS configuration. The process of 504-516 repeats to record a collection of CVs associated with each NS configuration. When the CV corresponds to AF burden, each collection of CVs represents a trend in AF burden associated with a particular NS configuration. The method will thus save AF burden trends for each NS configuration.

Optionally, the physiologic characteristic of interest may be something in addition to AF burden and/or a characteristic other than AF burden, such as AT burden, ST segment shift and the like. Hence, in this alternative example, the method of FIG. 5 would record a CV associated with each AT event or ST segment shift for each NS configuration. Each collection of CVs would represent a trend in AT burden or ST segment shift associated with a particular NS configuration. The method will thus save AT burden trends and/or ST segment shift trends for each NS configuration.

Returning to 514, once the set of potential NS configurations of interest has been utilized, flow moves to 518. At 518, the method analyzes the collection of CVs to obtain long term CV trends associated with each of the NS configurations. For example, the analysis may plot, in a timeline, the number or duration of each AF or AT episode, duration of cumulative AF burden over time, cumulative AT burden over time, a number or duration of ST segment shifts over time and the like. The analysis will determine trends in the CV over each time interval for which a given NS configuration is used. For example, when using one NS configuration, the patient may experience an increase in the AF burden over a 1 week period (e.g., number of AF episodes per day increases, length of each AF episode increases). When using a second NS configuration, the patient may experience a decrease in the AF burden over the next 1 week period (e.g., number of AF episodes per day decreases, length of each AF episode decreases).

At 520, the method selects the NS configuration for long term operation that corresponds to a desired trend. For example, if it is desirable to identify a trend in which a length of each AF episode is shortened, then the NS configuration would be selected that corresponds to the greatest decrease (e.g. percentage or minutes) in AF episode length between a beginning and an ending of when the particular NS configuration was used. For example, if it is desirable to identify a trend in which a number of AF episodes decreases, then the NS configuration would be selected that corresponds to the greatest decrease in the number of AF episode between a beginning and an ending of when the particular NS configuration was used. Optionally, the trend during a select NS configuration may be compared to a baseline trend when no NS configuration is used.

Optionally, the selection at 520 may be based on satisfying or being near a number of thresholds. For example, the NS configuration may be selected that is associated with the fewest number of AF episodes, the shortest length AF episodes, and the like.

The foregoing methods and systems afford feedback to aid in determining a desired NS electrode placement and configuration, to aid in trouble shooting lead migration issues, and to aid in assessing patient response to NS treatment acutely. For example, it may be determined that a new desired electrode combination is preferred that is shifted laterally (left or right) a few millimeters along a vertebra, or translated vertically up or down a few millimeters along the vertebra. It may be determined that a single row of active electrodes on one side or end of the lead yield the fastest return to a normal sinus rhythm. As another example, it may be determined that a wider distributed array of active electrodes (e.g., all electrodes are active, a checkerboard pattern of electrodes are active, etc.) may terminate AF in a desired manner.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method to control a configuration of a neural stimulation (NS) system having an NS device coupled to an NS lead, the method comprising:
   cycling through multiple predetermined potential NS configurations of the NS system;
   setting a timer associated with an amount of time for an arrhythmia related electrophysiology change to occur in response to at least one of the predetermined potential NS configurations;
   after the timer expires, collecting cardiac signals from a patient that are representative of cardiac rhythms experienced by the patient, the collecting operation in connection with each of the multiple predetermined potential NS configurations for a corresponding period of time;
   deriving, from the cardiac signals collected after the timer expires, characteristic values (CVs) for at least one physiologic characteristic indicative of at least one of normal and abnormal cardiac rhythms in connection with each of the corresponding multiple predetermined potential NS configurations; and
   then selecting, from the multiple predetermined potential NS configurations, an NS operating configuration to be used by the NS system based on the CVs.

2. The method of claim 1, wherein the collecting is performed over an extended period of time to obtain long-term diagnostic trends, the selecting operation further comprising assessing whether a long-term improvement is achieved when utilizing one or more of the NS operating configurations.

3. The method of claim 1, wherein the collecting is performed over an extended period of time sufficient to obtain a trend for AT/AF burden, the method further comprising identifying the trend for AT/AF burden, the selecting operation selecting the NS operating configuration based on the trend for AT/AF burden that is identified.

4. The method of claim 1, wherein the cycling through the predetermined potential NS configurations is performed automatically at predetermined time periods of interest.

5. The method of claim 1, wherein the selecting includes identifying a select characteristic value that satisfies a predetermined condition and determining a one of the predetermined potential NS configurations that is associated with the select characteristic value.

6. The method of claim 1, further comprises maintaining a one to one relation between the characteristic values that are derived and one of the predetermined potential NS configurations that was operative at the time when the cardiac signals associated with the characteristic values were collected.

7. The method of claim 1, further comprising determining that the cardiac rhythm exhibits an arrhythmia, and directing the NS device to begin operation with one of the predetermined potential NS configurations in response to the determination that the cardiac rhythm exhibits an arrhythmia.

8. The method of claim 1, wherein the deriving includes determining a characteristic value for at least one of an acute cardiac rhythm characteristic and a chronic cardiac rhythm characteristic.

9. The method of claim 1, wherein the deriving includes determining a characteristic value for at least one of the following physiologic characteristics: restoration time, R-R interval, P-P interval, R-wave regularity, P-wave regularity, dominate frequency of atrial fibrillation (AF), AF rate, AF regularity, Peak atrial rate, and a ratio of a number of ventricular events per set of atrial events.

10. The method of claim 1, wherein the cycling includes switching, after a predetermined time period of interest, between at least one of i) first and second electrode combinations, ii) first and second stimulus patterns, and iii) first and second active electrode placements, utilized to deliver an NS therapy from the NS lead.

11. The method of claim 1, wherein the cycling includes switching, after a predetermined time period of interest, between first and second stimulus patterns utilized to deliver an NS therapy from the NS lead.

12. The method of claim 1, wherein the cycling includes changing, after a predetermined time period of interest, a configuration value of at least one configuration parameter from the set of configuration parameters that includes stimulus phase, frequency, pulse width, pulse amplitude, number of active electrodes, active electrode pattern, active electrode position within electrode array, active electrode placement with respect to a reference anatomy.

13. The method of claim 1, further comprising sensing the cardiac signals, the cardiac signals representing one of intrathoracic electrogram signals, electrocardiogram signals, heart sound signals, blood pressure signals, and blood oxygen content signals.

14. The method of claim 1, wherein the timer is associated with a predetermined time period representing at least one time constant associated with the arrhythmia related electrophysiology change that occurs while the NS device operates in accordance with the current one of the predetermined potential NS configurations.

15. The method of claim 1, wherein the setting operation includes setting at least two different timers in connection with at least two different arrhythmia related electrophysiology changes that occur in response to the predetermined potential NS configurations.

16. The method of claim 1, wherein the timer corresponds to a first time constant related to an amount of time needed after delivery of an NS therapy with a current one of the predetermined potential NS configurations before stabilization of local circuit neurons of an intrinsic cardiac nervous system (ICN).

17. The method of claim 16, wherein the timer corresponds to a second time constant related to an amount of time before triggering centrally-mediated reflexes (TMR) occurs.

18. The method of claim 1, wherein the cycling, setting, waiting, and deriving operations are performed during a first iteration while the timer is set to a first time constant, and then the cycling, setting, waiting and deriving operations are repeated during a second iteration while the timer is set to a second time constant.

19. The method of claim 1, wherein the timer is set to different first and second time constants associated with stabilization of local circuit neurons of an intrinsic cardiac nervous system (ICN) and triggering centrally-mediated reflexes (TMR), respectively.

20. A neural stimulation (NS) system, comprising:
   an NS device coupled to an NS lead;
   memory configured to save multiple predetermined potential NS configurations;
   a controller configured to direct the NS device to cycle through each of the multiple predetermined potential NS configurations, the controller configured to set a timer associated with an amount of time for an arrhythmia related electrophysiology change to occur in response to at least one of the predetermined potential NS configurations and to collect cardiac signals after the timer expires;

inputs configured to receive the cardiac signals that are collected from a patient over a period of time during which each of the multiple predetermined potential NS configurations is utilized, the cardiac signals being representative of cardiac rhythms experienced by the patient;

a cardiac signal analysis (CSA) module configured to derive, from the cardiac signals collected after the time expires, characteristic values (CVs) for at least one physiologic characteristic indicative of at least one of normal and abnormal cardiac rhythms that occur while the NS device operates in each of the corresponding multiple predetermined potential NS configurations; and a CV analysis module configured to analyze the multiple CVs and then select, from the multiple predetermined potential NS configurations, an NS operating configuration to be used by the NS system based on the CVs.

21. The system of claim 20, wherein the inputs receive cardiac signals over an extended period of time and the CV analysis module analyzes the CVs to obtain long-term diagnostic trends, the CV analysis module configured to assess whether a long-term improvement is achieved when utilizing one or more of the NS operating configurations.

22. The system of claim 20, wherein the CV analysis module analyzes AT/AF burden experienced by the heart and obtains a trend for AT/AF burden, the CV analysis module selects the NS operating configuration based on the trend for AT/AF burden.

23. The system of claim 20, wherein the controller cycles from one of the multiple predetermined potential NS configurations to another of the multiple predetermined potential NS configurations based on at least one of i) automatically after a predetermined time period of interest and ii) the physiologic characteristic of the cardiac signals, the physiologic characteristic representing AT/AF burden, the memory recording the characteristic values for AT/AF burden exhibited during each of the predetermined time periods of interest.

24. The system of claim 20, wherein the CV analysis module identifies a select characteristic value that satisfies a predetermined condition and determines one of the predetermined potential NS configurations that is associated with the select characteristic value.

25. The system of claim 20, wherein the memory maintains a one to one relation between the characteristic values that are derived and a one of the predetermined potential NS configurations that was operative at the time when the cardiac signals associated with the characteristic values were collected.

26. The system of claim 20, wherein the controller is configured to direct the NS device to begin operation with one of the multiple predetermined potential NS configurations in response to a determination that the cardiac rhythm exhibits an arrhythmia.

27. The system of claim 20, wherein the CSA module determines a characteristic value for at least one of an acute cardiac rhythm characteristic and a chronic cardiac rhythm characteristic.

28. The system of claim 20, wherein the CSA module determines a characteristic value for at least one of the following physiologic characteristics: restoration time, R-R interval, P-P interval, R-wave regularity, P-wave regularity, dominate frequency of atrial fibrillation (AF), AF rate, AF regularity, Peak atrial rate, and a ratio of a number of ventricular events per set of atrial events.

29. The system of claim 20, wherein the controller changes the predetermined potential NS configuration by switching, after a predetermined time period of interest, between at least one of i) first and second electrode combinations, ii) first and second stimulus patterns, and iii) first and second active electrode placements, utilized to deliver an NS therapy from the NS lead.

30. The system of claim 20, wherein the controller changes the predetermined potential NS configuration by switching, after a predetermined time period of interest, between first and second stimulus patterns utilized to deliver an NS therapy from the NS lead.

31. The system of claim 20, wherein the controller changes the predetermined potential NS configuration, after a predetermined time period of interest, by changing a configuration value of at least one configuration parameter from the set of configuration parameters that includes stimulus phase, frequency, pulse width, pulse amplitude, number of active electrodes, active electrode pattern, active electrode position within electrode array, active electrode placement with respect to a reference anatomy.

32. The system of claim 20, further comprising a sensor coupled to the input, the sensor configured to collect cardiac signals that represent one of intra-thoracic electrogram signals, electrocardiogram signals, heart sound signals, blood pressure signals, and blood oxygen content signals.

33. The system of claim 20, wherein the timer is associated with a predetermined time period representing at least one time constant associated with the arrhythmia related electrophysiology change that occurs while the NS device operates in accordance with the current one of the predetermined potential NS configurations.

34. The system of claim 20, wherein the controller sets at least two different timers in connection with at least two different arrhythmia related electrophysiology changes that occur in response to the predetermined potential NS configurations.

35. The system of claim 20, wherein the timer corresponds to a first time constant related to an amount of time needed after delivery of an NS therapy with a current one of the predetermined potential NS configurations before stabilization of local circuit neurons of an intrinsic cardiac nervous system (ICN).

36. The system of claim 35, wherein the timer corresponds to a second time constant related to an amount of time before triggering centrally-mediated reflexes (TMR) occurs.

37. The system of claim 20, wherein the controller and CAS module perform the cycling, setting, waiting, and deriving operations during a first iteration while the timer is set to a first time constant, and then repeat the cycling, setting, waiting and deriving operations during a second iteration while the timer is set to a second time constant.

38. The system of claim 20, wherein the timer is set to different first and second time constants associated with stabilization of local circuit neurons of an intrinsic cardiac nervous system (ICN) and triggering centrally-mediated reflexes (TMR), respectively.

* * * * *